(12) United States Patent
Levitz et al.

(10) Patent No.: US 11,448,250 B2
(45) Date of Patent: Sep. 20, 2022

(54) CONNECTOR WITH SHAFT AND CYLINDRICAL BASE EXTENDING FROM FLANGE

(71) Applicant: Altria Client Services LLC, Richmond, VA (US)

(72) Inventors: Robert Levitz, North Miami Beach, FL (US); Shmuel Gavrielov, North Miami Beach, FL (US)

(73) Assignee: Altria Client Services LLC, Richmond, VA (US)

( * ) Notice: Subject to any disclaimer, the term of this patent is extended or adjusted under 35 U.S.C. 154(b) by 63 days.

(21) Appl. No.: 17/066,664

(22) Filed: Oct. 9, 2020

(65) Prior Publication Data

US 2021/0022394 A1   Jan. 28, 2021

Related U.S. Application Data

(60) Division of application No. 15/980,329, filed on May 15, 2018, now Pat. No. 10,798,973, which is a
(Continued)

(51) Int. Cl.
*F16B 7/04* (2006.01)
*F16B 7/18* (2006.01)
(Continued)

(52) U.S. Cl.
CPC ............ *F16B 7/0413* (2013.01); *A24F 40/40* (2020.01); *A24F 40/90* (2020.01); *A61M 11/042* (2014.02);
(Continued)

(58) Field of Classification Search
CPC ... A24F 47/002; A24F 47/008; A61M 11/042; A61M 15/06; A61M 2016/0021;
(Continued)

(56) References Cited

U.S. PATENT DOCUMENTS 272,315 A    2/1883 Pease
1,542,266 A  6/1925 Palmer
(Continued)

FOREIGN PATENT DOCUMENTS

CA    2641869 A1    5/2010
CN   201238610 Y   5/2009
(Continued)

OTHER PUBLICATIONS

International Search Report and Written Opinion of the International Searching Authority for corresponding PCT Application No. PCT/US2012/033329 dated Oct. 4, 2012.
(Continued)

*Primary Examiner* — Josh Skroupa
(74) *Attorney, Agent, or Firm* — Harness, Dickey & Pierce, P.L.C.

(57) ABSTRACT

The connector is configured to couple a first section and a second section of an e-vaping device, and the connector includes a flange with a first end and a second end, a shaft extending from the first end of the flange, an outer shelf being formed by a portion of the first end of the flange, a cylindrical base extending from the second end of the flange, and an inner shelf within the connector, the cylindrical base and the inner shelf at least partially defining a longitudinal opening, the flange defining at least one first notch, the at least one first notch at least partially along the second end of the flange.

21 Claims, 10 Drawing Sheets

Related U.S. Application Data division of application No. 15/492,290, filed on Apr. 20, 2017, now Pat. No. 9,999,257, which is a continuation of application No. 14/051,029, filed on Oct. 10, 2013, now Pat. No. 9,675,107, which is a continuation of application No. PCT/US2012/033329, filed on Apr. 12, 2012.

(60) Provisional application No. 61/474,569, filed on Apr. 12, 2011.

(51) Int. Cl.

| | | |
|---|---|---|
| *A61M 15/06* | (2006.01) | |
| *A61M 11/04* | (2006.01) | |
| *A24F 40/40* | (2020.01) | |
| *A24F 40/90* | (2020.01) | |
| *H01R 33/22* | (2006.01) | |
| *A61M 16/00* | (2006.01) | |

(52) U.S. Cl.
CPC ........... *A61M 15/06* (2013.01); *F16B 7/0446* (2013.01); *F16B 7/182* (2013.01); *H01R 33/22* (2013.01); *A61M 2016/0021* (2013.01); *A61M 2016/0039* (2013.01); *A61M 2205/3653* (2013.01); *A61M 2205/42* (2013.01); *A61M 2205/8206* (2013.01); *Y10T 403/255* (2015.01); *Y10T 403/556* (2015.01); *Y10T 403/559* (2015.01); *Y10T 403/56* (2015.01)

(58) Field of Classification Search
CPC .. A61M 2016/0039; A61M 2205/3653; A61M 2205/42; A61M 2205/8206; F16B 7/0406–0426; F16B 7/0446; F16B 7/182; Y10T 403/25; Y10T 403/255; Y10T 403/55; Y10T 403/556; Y10T 403/559; Y10T 403/56; Y10T 403/561; Y10T 403/68; Y10T 403/7026
USPC ........... 403/34, 37, 292, 296, 298, 309, 343, 403/359.1, 299
See application file for complete search history.

(56) References Cited

U.S. PATENT DOCUMENTS

| | | | |
|---|---|---|---|
| 3,425,414 | A | 2/1969 | La Roche |
| 3,797,865 | A | 3/1974 | Ballentine |
| 3,957,064 | A | 5/1976 | Camps Mestre et al. |
| 4,655,630 | A | 4/1987 | Rinehart |
| 4,657,008 | A | 4/1987 | Broddner et al. |
| 4,700,420 | A | 10/1987 | Belanger |
| 4,771,796 | A | 9/1988 | Myer |
| 4,947,875 | A | 8/1990 | Brooks et al. |
| 5,042,510 | A | 8/1991 | Curtiss et al. |
| 5,067,500 | A | 11/1991 | Keritsis |
| 6,167,880 | B1 | 1/2001 | Gonda et al. |
| 6,196,219 | B1 | 3/2001 | Hess et al. |
| 6,923,175 | B2 | 8/2005 | Poole et al. |
| 8,851,068 | B2 | 10/2014 | Cohen et al. |
| 8,851,083 | B2 | 10/2014 | Oglesby et al. |
| 9,132,248 | B2 | 9/2015 | Qiu |
| 2005/0016550 | A1 | 1/2005 | Katase |
| 2009/0095311 | A1 | 4/2009 | Han |
| 2009/0272379 | A1 | 11/2009 | Thorens et al. |
| 2010/0024834 | A1 | 2/2010 | Oglesby et al. |
| 2011/0036346 | A1 | 2/2011 | Cohen et al. |
| 2011/0290244 | A1* | 12/2011 | Schennum .............. A24F 42/60 128/200.23 |
| 2013/0192618 | A1 | 8/2013 | Li et al. |
| 2013/0255702 | A1 | 10/2013 | Griffith, Jr. et al. |
| 2014/0338680 | A1* | 11/2014 | Abramov ................ A24F 40/46 131/328 |

FOREIGN PATENT DOCUMENTS

| | | |
|---|---|---|
| CN | 201430916 Y | 3/2010 |
| CN | 101843368 A | 9/2010 |
| CN | 101869356 A | 10/2010 |
| CN | 201750712 U | 2/2011 |
| CN | 201767029 U | 3/2011 |
| CN | 201781984 U | 4/2011 |
| DE | 202006013439 U1 | 10/2006 |
| EP | 2805636 A2 | 11/2014 |
| JP | 2009-537119 A | 10/2009 |
| JP | 3160708 U | 7/2010 |
| JP | 2010-213579 A | 9/2010 |
| JP | 2012124081 A | 6/2012 |
| KR | 20100004364 U | 4/2010 |
| KR | 20100011034 U | 11/2010 |
| KR | 200452359 Y1 | 2/2011 |
| WO | WO-9843019 A1 | 10/1998 |
| WO | WO-2001068169 A1 | 9/2001 |
| WO | WO-2013116571 A1 | 8/2013 |

OTHER PUBLICATIONS

International Preliminary Report on Patentability for corresponding PCT Application No. PCT/US2012/033329 dated Oct. 15, 2013.
Search Report for European Application No. 14170502.0 dated Feb. 25, 2015.
Office Action from corresponding Chinese Patent Application No. 201280018281.2, dated Jul. 1, 2015.
Supplementary European Search Report dated Feb. 12, 2015 for Application No. EP 12 77 1732.
Office Action from corresponding Japanese Patent Application 2014-505283, dated Jan. 18, 2016.
Specification Translation of CN201072979, Li, Yonghai, Atomizer used for electronic cigarette, Jun. 18, 2008.
Specification Translation of CN101843368, Chen, Zhiping. Suction nozzle of electronic atomizer, Sep. 29, 2010.
Office Action from U.S. Appl. No. 14/051,029, dated Mar. 2, 2016.
Office Action from U.S. Appl. No. 14/051,029, dated Jun. 2, 2016.
Office Action from U.S. Appl. No. 14/051,029, dated Dec. 7, 2016.
Notice of Allowance from U.S. Appl. No. 14/051,029, dated Feb. 15, 2017.
Extended European Search Report dated Feb. 25, 2015 for European Application No. 12771732.

* cited by examiner

CONNECTOR WITH SHAFT AND CYLINDRICAL BASE EXTENDING FROM FLANGE

PRIORITY CLAIM

This application is a Divisional of U.S. application Ser. No. 15/980,329, filed May 15, 2018, which is a Divisional of U.S. application Ser. No. 15/492,290, filed Apr. 20, 2017, which is a Continuation of U.S. application Ser. No. 14/051,029, filed Oct. 10, 2013, which claims priority as a Continuation to PCT Application No. PCT/US2012/033329, filed on Apr. 12, 2012, which claims priority to U.S. Provisional Patent Application No. 61/474,569, filed on Apr. 12, 2011, the disclosures of each of which are incorporated by reference in their entirety.

BACKGROUND

Field

This invention relates generally to electronic cigarettes and more specifically to a battery connector for an electronic cigarette having a side air intake for improved air in-flow and out-flow through the electronic cigarette.

Related Art

Electronic cigarettes are becoming a popular alternative to tobacco smoking because of the many advantages that they offer. One of the main reasons that they are popular is due to their similarities to tobacco smoking. In fact, the closer that they are in providing the experience of a traditional cigarette, the more likely they are to be accepted in the market place.

An electronic cigarette typically comprises a battery, an atomizer, a container of smoke juice, a heating element and a power control circuit. The battery is used to power the circuit and the atomizer, where the atomizer heats the smoke juice to create smoke or vapor, which is inhaled by a user.

One example of an electronic cigarette (hereinafter an "Electronic Cigarette" or "E-cigarette") is a "two-piece" device having a first battery section and a second atomizer section, wherein the atomizer section is detachable from the battery section.

An example of one such Electronic Cigarette is shown in FIGS. 1 and 2. In some embodiments, the battery section B contains a power cell, an airflow sensor, and a chipset (hereinafter referred to as, the Battery). In some embodiments, the atomizer section A contains a heating element and a container of "smoke juice" which comprises flavorings and a vaporizing base, such as glycol (hereinafter referred to as a "Cartomizer"). Typically, the Battery and Cartomizer are physically and electrically connected by a threaded engagement. In some embodiments, the Battery has the "male" threaded portion and the Cartomizer has the "female" threaded portion, as shown in FIG. 2.

In the beginning stages of development of the Electronic Cigarette, it was natural to copy the air flow and to mimic its path similar to the way it behaves in a traditional cigarette. In a tobacco cigarette, air enters the tip, which collects the smoke and enters the smoker's mouth through the "filter." Likewise, early E-cigarettes had one or more notches at the tip of the Battery to allow air intake. Air would enter from the tip, pass through the entire Battery, and continue through the Cartomizer, the vapor-producing portion of the E-cigarette, and enter the smoker's mouth via the distal end of the Cartomizer, which functions as a mouth piece.

A cross-section of an example of this arrangement can be seen in FIG. 3. As shown in FIG. 3, when air 104 is inhaled through the mouthpiece 100, air enters the tip of the cigarette, travels past an air flow sensor 102 through the spaces provided around the sensor 102, and continues past the battery B (in this case a lithium cell.) It then goes through the opening in the axis of a post engaged with the Battery's male connector 106, and straight into a post 108 engaged to the female connector of the Cartomizer. The air is then inundated with atomized particles of liquid vapor and exits through the mouthpiece of the Cartomizer into the smoker's mouth.

Heretofore, there has often been a specific problem with tip-intake Electronic Cigarettes that the present invention aims to eliminate. When the smoker exhales into a tip-intake battery Electronic Cigarette (as smokers often do), the vapors 104A from the mouth follow the reverse of the path described above—they flow inside the Battery towards the sensor and often condense causing the sensor to become clogged and fail. The exhalation likewise causes excess liquid in the Cartomizer to follow the same path into the Battery part towards the sensor, clogging it further and also causing it to fail. This also causes major difficulties in mass-production in terms of maintaining consistent air flow and consistent sensitivity of the sensor from one Electronic Cigarette to the next.

Therefore it is desirable to avoid bringing the intake air through the entire length of the Battery through its rear tip (hereinafter "Tip-Intake"), and instead to bring it in through its front side (hereinafter "Side-Intake"), at the point where the Battery and Cartomizer sections meet.

However, it was always perceived as a necessity for the female threaded portion of the Cartomizer to have air slits at its edges when used in conjunction with a Side Intake Battery, because it was otherwise difficult to mass-produce machined male threads that allow air intake at its base. As a result, if it was desirable to change the design of the E-cigarette from the Tip-Intake type to the Side-Intake type, one would necessarily need to modify the female portion of the E-cigarette, i.e. the Cartomizer. Therefore, if it was desirable to make slits on the Battery section of the E-cigarette, one would need to redesign the entire E-cigarette so that the Battery section would be the female threaded portion and the Cartomizer section would be the male threaded portion. Additionally, one could never offer an option of interchanging the male Battery section between the Tip-Intake type with the Side-Intake type, while maintaining compatibility with the same female portion, since in the latter, the female Cartomizer would require slits at the engagement point, whereas in the former, the female Cartomizer could not have slits, otherwise the resulting airflow through the E-cigarette would be too great.

Accordingly, implementation of a Side-Intake Electronic Cigarette has, until the present invention, been considered an expensive and complicated proposition which would, by necessity, require redesign of all parts of the device and eliminate the possibility of backwards-compatibility of the majority of internal parts of the device.

SUMMARY

The present invention resolves the above problems and provide an air intake path from the side of the E-cigarette via modification to the male Battery connector, without modifying the female Cartomizer connector, while maintaining ease of manufacture—especially ease of machining the male Battery connector during mass production, and backwards compatibility whereas the same un-slited female Cartomizer could be used together with the male Battery connector for both the Tip-Intake and Side-Intake types of E-cigarettes.

The present invention also provides the possibility to create an air path that will allow a silent air intake, unlike other Side-Intake solutions that generate substantial hissing noise as the air enters from the side.

A cross-section of an Electronic Cigarette utilizing the Battery connector of the present invention is shown in FIG. 4. As can be seen there, the spaces 110 around the sensor are blocked so no air flow takes place through the cavity of the battery part. During inhalation, air 104 enters from the side 112 of the Battery and enters the post 108 of the Battery B via a groove in the battery post. It then enters into the Cartomizer A through the axial opening in the Cartomizer post and exits the Cartomizer into the smoker's mouth. Although there is also provided an opening 114 into the Battery through the battery post, there is minimal air or vapor flow through said opening 114 (hereinafter "pressure differential channel" 114) because the spaces 110 around the sensor are blocked. As a result, during inhalation, the sensor 102 can detect a pressure differential via said pressure differential channel 114.

During exhalation, the vapors do not enter into the battery part towards the sensor; they travel out through the side vents, opposite to the direction that air entered upon inhalation. Such a construction greatly extends the life of the product.

DETAILED DESCRIPTION

Figure 1:
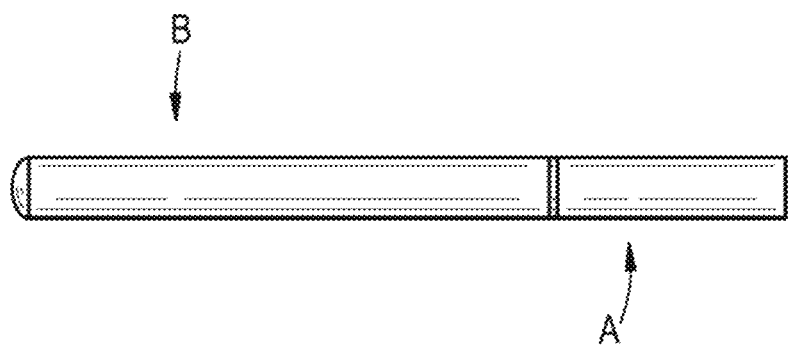
FIG. 1 is an assembled view of a typical two-piece electronic cigarette.
Figure 2:
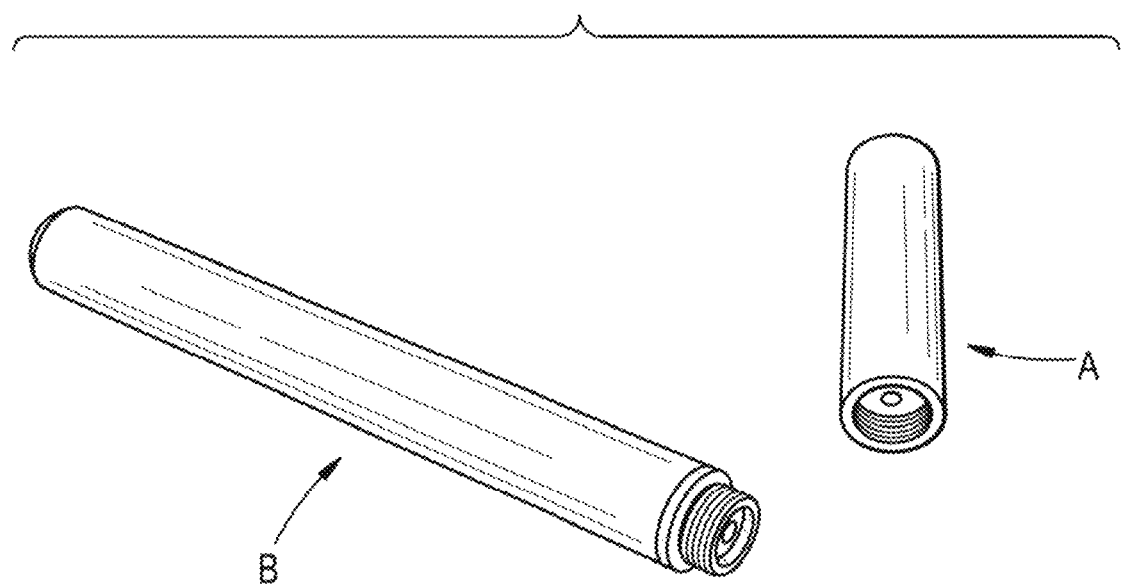
FIG. 2 is a disassembled view of a typical two-piece electronic cigarette.
Figure 3:
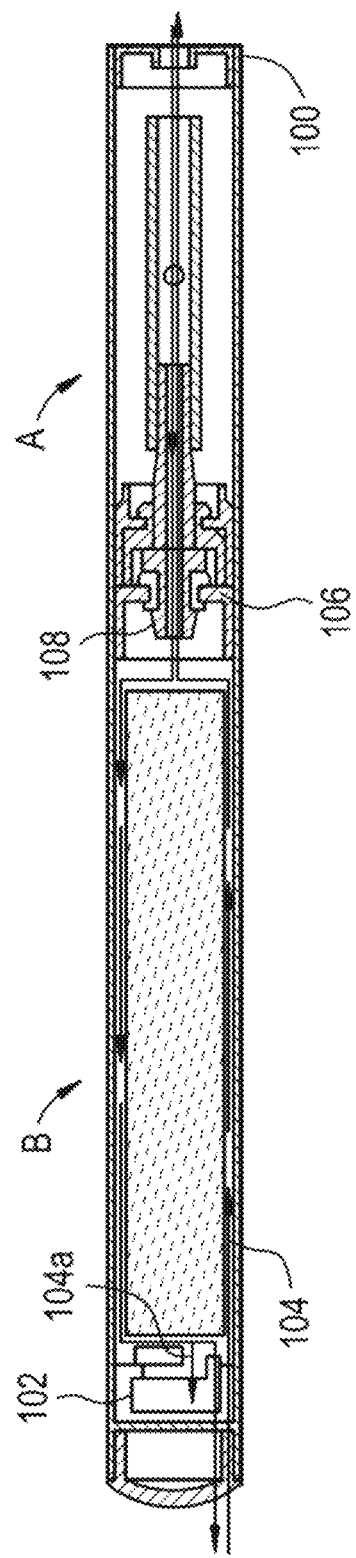
FIG. 3 is a cross-sectional view of an electronic cigarette in the prior art showing inhaled and exhaled air paths.
Figure 4:
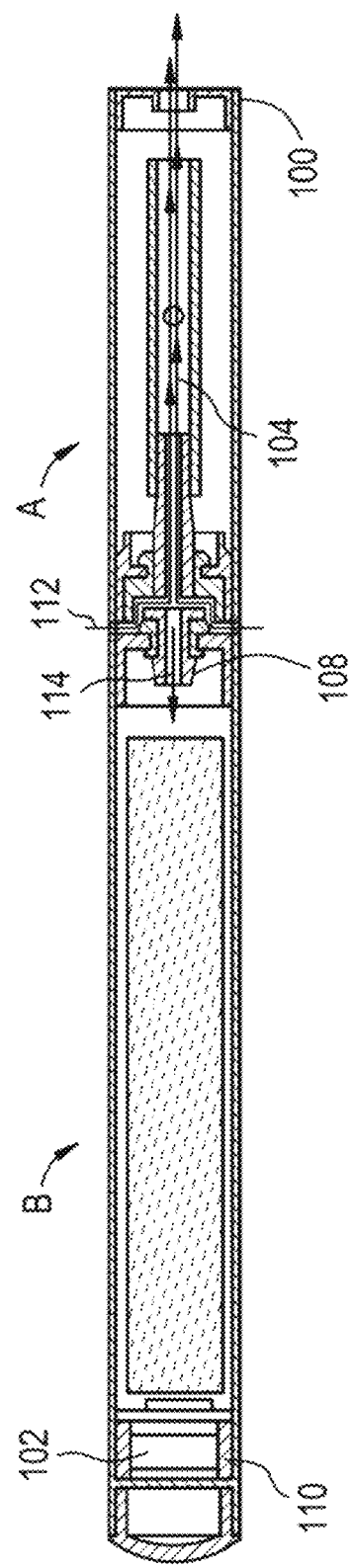
FIG. 4 is a cross-sectional view of an electronic cigarette using the novel connector herein described showing inhaled and exhaled air paths.

The present invention concerns various embodiments of a Battery-Cartomizer connector for an Electronic Cigarette that creates an air-intake path that enters through the male connector (i.e. the Battery section), without the need to modify the female connector (i.e. the Cartomizer section) thereof. Accordingly, the present invention permits flexibility of design and product diversification for the E-cigarette manufacturer, maintains ease of manufacture and mass-production, and creates additional advantages such as reducing noise and hissing during air-intake (i.e. a "puff or "drag").

FIGS. 5-13 depict various embodiments of the connector of the present invention. It is understood that these figures depict a sectional view of an E-cigarette connector 1, which joins the Battery section to the Cartomizer section by a threaded engagement. As shown in FIGS. 5-13, it is intended that the male Battery connector M at the proximal end 3 of the connector mates to a female portion of a Cartomizer, and the distal end 5 of the connector is attached, through a pressure or friction fit, or through other suitable means, to the Battery portion B (not shown) and functions as a "cap" thereof.

In some embodiments of the present invention, an air intake path starts at the outer circumference of the connector 1 between the Battery and the Cartomizer of the E-cigarette, running inside notch 9 on connector 1. The air is thus brought into the Battery through grooves 10 formed on the attachment (i.e., non-threaded) distal end 5 of the connector. Once inside the battery, the air path loops around and exits the Battery housing towards the Cartomizer, via a hole along the central axis of connector 1. In accordance with the desired air-intake path, notch 9 is cut out on the side of connector 1 at strategic location and with strategic geometry.

In most E-cigarettes, connector 1 has a flange 7 that appears from the outside as a metallic ring when the separate parts of the E-cigarette are screwed together, like that shown in FIG. 1. The resulting ring is usually very thin, and has little purpose other than cosmetic—to create a decorative divider between the two major parts of the E-cigarette (i.e. the Battery section and the Cartomizer section) and to cover the inside edge of the Battery housing. Cutting into this ring or removing a portion of it to create the desired air-intake characteristics of the present invention would expose the dull edge of the Battery housing and detracts from the esthetics of the product. However, in some embodiments of the present invention, the thickness of the flange is increased so that a portion of it can be cut or milled away, resulting in notch 9, while the remaining portion of the flange thickness will still retain the aesthetic design and still cover the internal edge of the housing.

Figure 5:
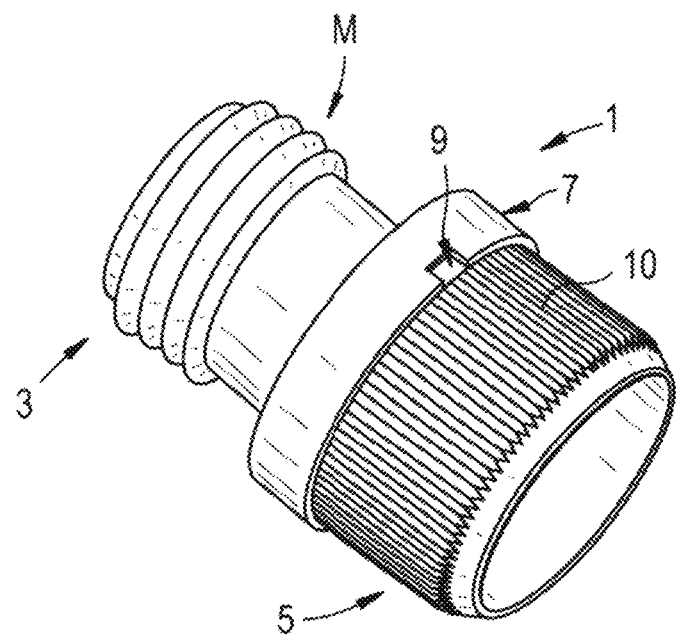
FIGS. 5-13 are alternative embodiments of the connector of the present invention showing various arrangements of side vent apertures.

Accordingly, as shown in FIG. 5, in some embodiments of connector 1, notch 9 begins at the outer perimeter of the flange 7, toward distal end 5 and travels toward the center axis of flange 7, resulting in a rectangular shape.

Figure 6:
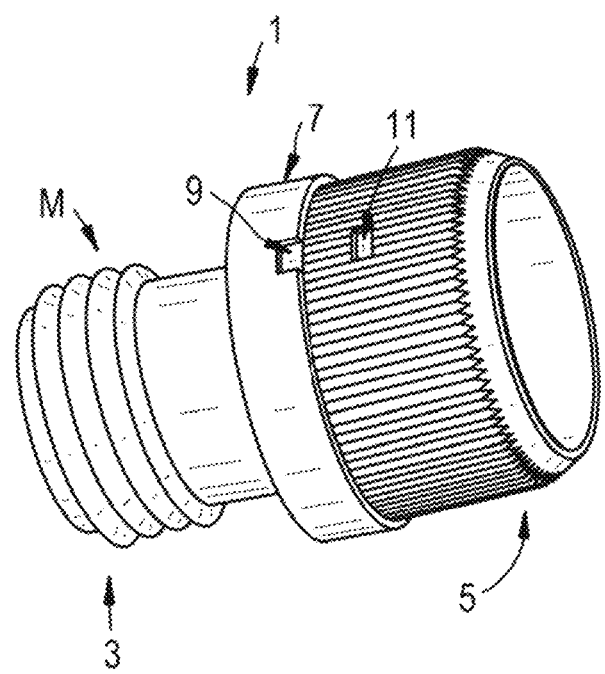

In some embodiments, such as in FIG. 6, aperture 11 is bored through the wall of the distal end 5 of connector 1 at substantially the same radial location as notch 9. This configuration increases the air-intake volume, permitting less-constricted air flow through the connector 1 and the Battery section.

Figure 7:
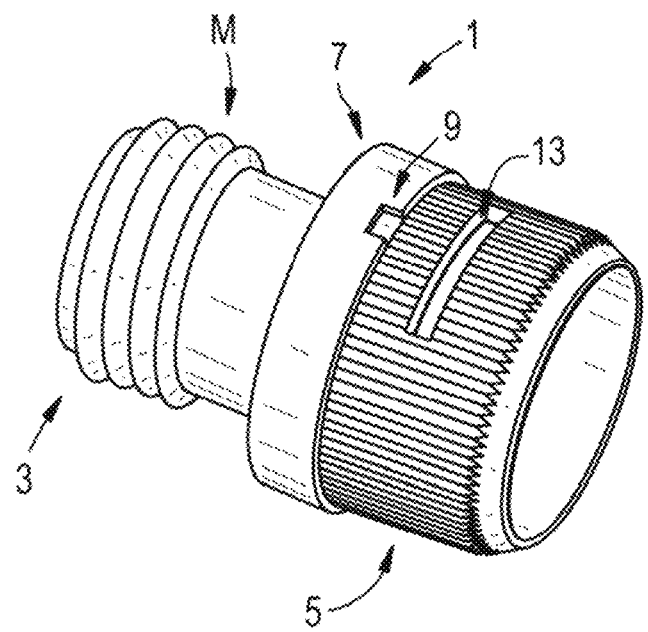

In some embodiments, such as in FIG. 7, slot 13 is milled along the curved wall of the distal end 5 of connector 1, with notch 9 located substantially across from the center of slot 13, radially. As shown, slot 13 is oriented perpendicular to the longitudinal axis of connector 1.

Figure 8:
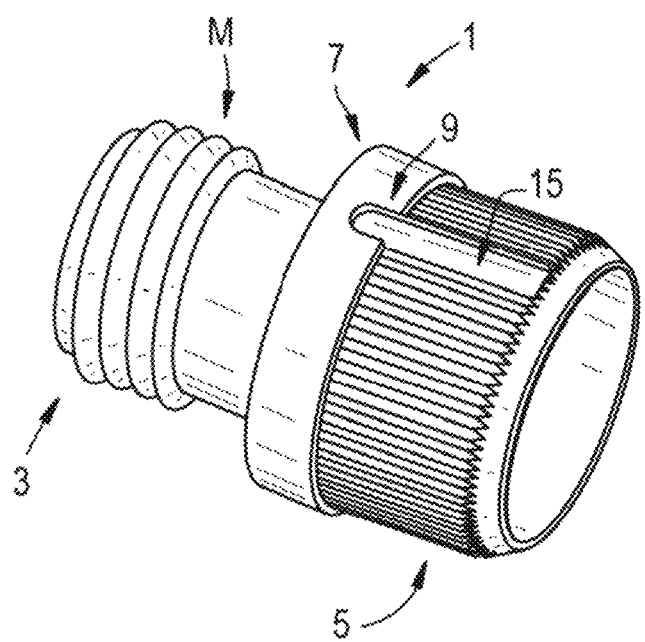

In some embodiments, such as in FIG. 8, channel 15 is milled across the outer surface of the distal end 5 of connector 1, beginning at notch 9 and terminating at the end of distal end 5. In this configuration, notch 9 has a substantially curved profile that transitions uniformly into channel 15. In this configuration, channel 15 is milled substantially parallel to the longitudinal axis of connector 1.

Figure 9:
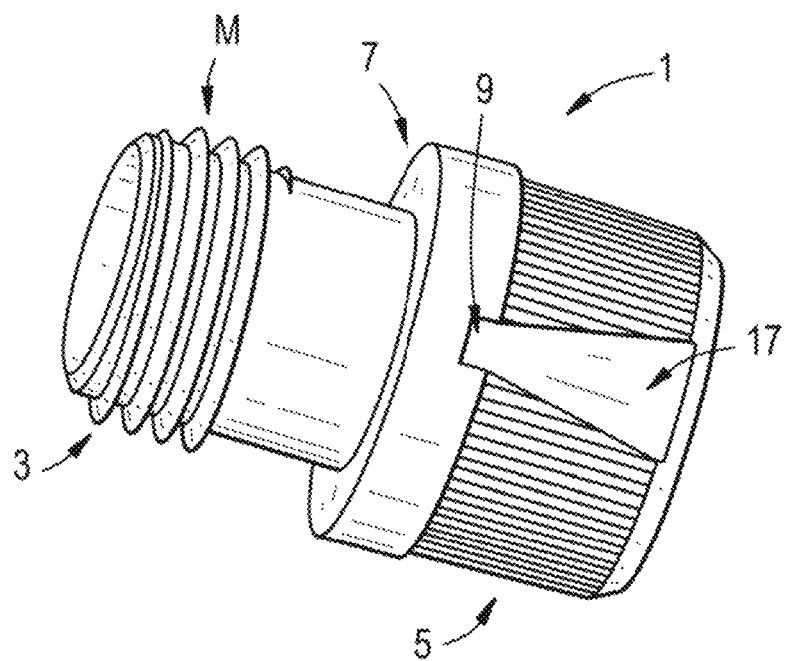

In some embodiments, such as in FIG. 9, fanned channel 17 is milled across the outer surface of the distal end 5 of connector 1, beginning at notch 9 and terminating at the end of distal end 5. Notch 9 has a substantially curved profile that transitions into fanned channel 17. Fanned channel 17 is milled substantially parallel to the longitudinal axis of connector 1.

Figure 10:
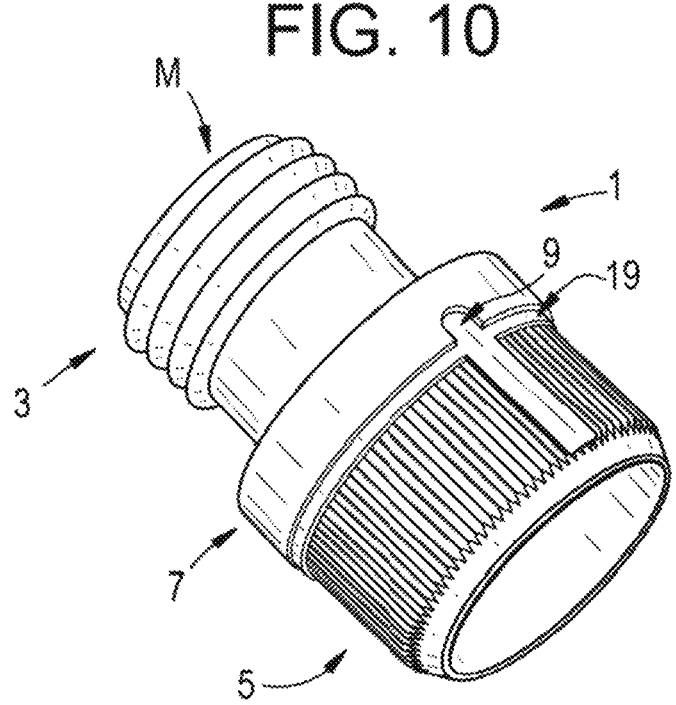

In some embodiments, such as in FIG. 10, channel 19 is milled away all around the outer circumference of flange 7, along its distal edge. The purpose of channel 19 is to allow for air intake even when a user happens to hold his finger over notch 9 during smoking. When that happens, air enters channel 19 and runs along the channel until it reaches and enters notch 9.

Figure 11:
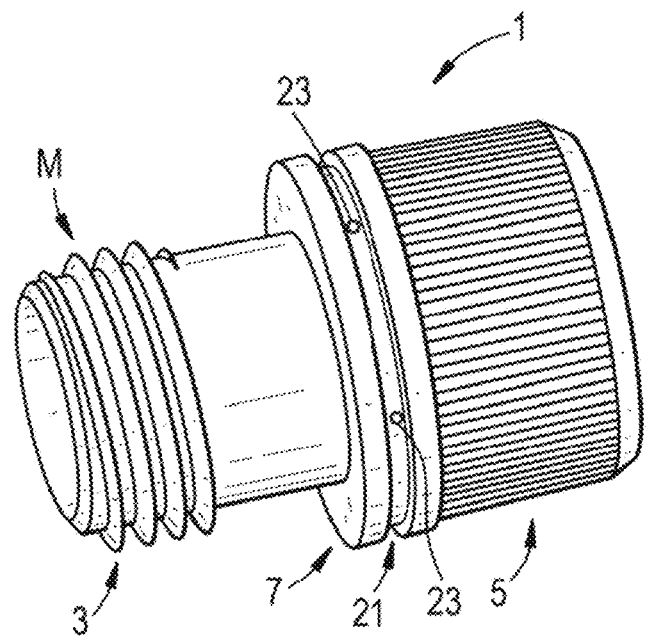

In some embodiments, such as in FIG. 11, channel 21 is milled away all around the outer circumference of flange 7, substantially in the middle of the flange. Several apertures 23 are bored through the wall of the flange. The purpose of channel 21 is to allow for air intake even when a user holds his finger over an aperture 23 during smoking. When that happens, air enters channel 21 and runs along the channel until it reaches and enters an aperture 23.

Figure 12:
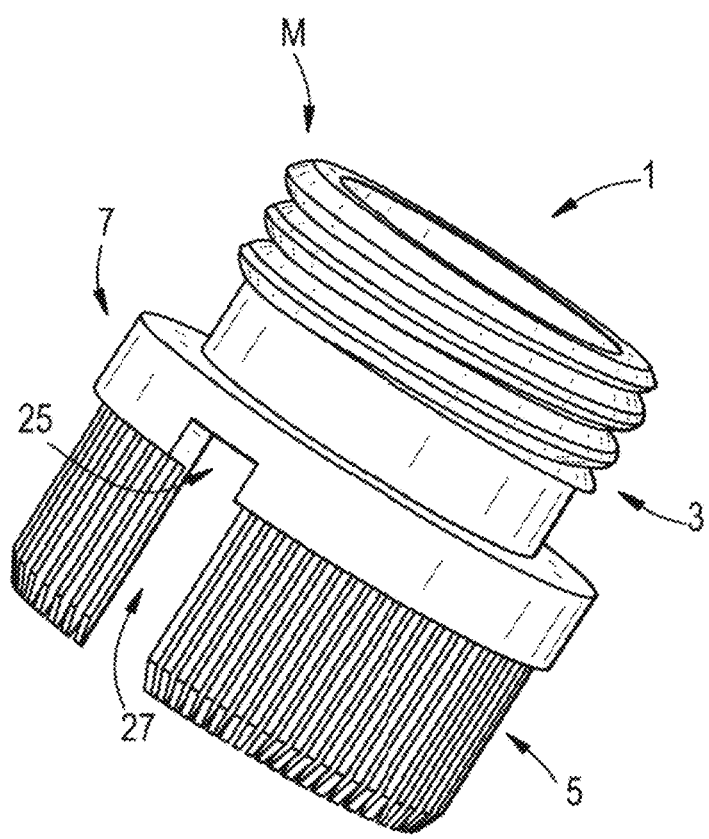

In some embodiments, such as in FIG. 12, notch 25 is cut out through the wall of flange 7 on the side of connector 1 at strategic location and with strategic geometry. Slot 27 is cut out of the distal end 5 of connector 1, beginning at notch 25 and terminating at the end of distal end 5. In this configuration, notch 25 has a rectangular profile that transitions uniformly into slot 27.

Figure 13:
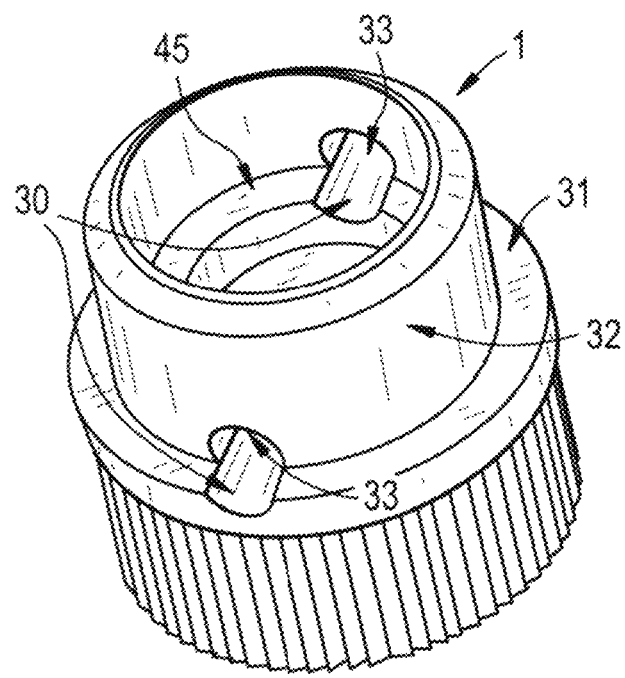
Figure 14:
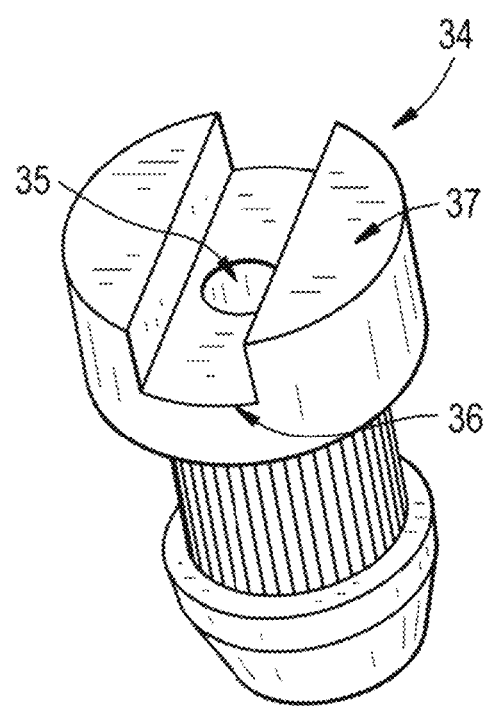
FIGS. 14-15 illustrate an alternative embodiment of a connector of the present invention with a battery post of the present invention.
Figure 15:
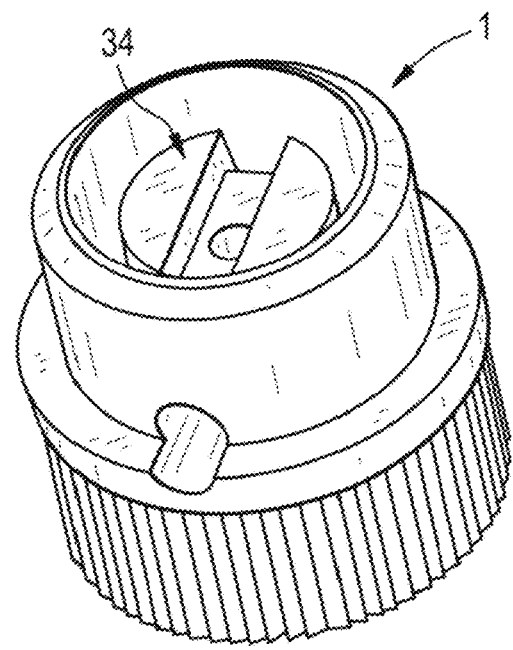

Another embodiment of the connector of the present invention is shown in FIGS. 13-15. FIG. 13 shows the connector without a battery post, FIG. 14 shows the battery post and FIG. 15 shows the battery post and connector assembled. As shown in FIG. 13, instead of a notch in the outer perimeter of the flange 7, toward distal end 5, perpendicular surface channels 30 are drilled on shelf 31 of flange 7. The channels continue and penetrate through the shaft 32 of connector 1 (in which threads are not shown for purposes of clarity) at orifices 33 and continue through inner shelf 45. The engaging battery post 34, shown in FIG. 14, includes a longitudinal orifice 35 (beginning on the surface of post head 37 and continuing longitudinally completely through the post) that forms the pressure differential channel, as well as a groove 36 which assists in guiding air inhaled or exhaled through perpendicular surface channel 30 and orifice 33.

It should be noted here that although in FIG. 15 groove 36 is shown aligned with perpendicular surface channel 30 and orifice 33, because the outer diameter of post head 37 is smaller than the inner diameter of shaft 32, such alignment is not necessary to allow for unimpeded air flow through connector 1.

Figure 16:
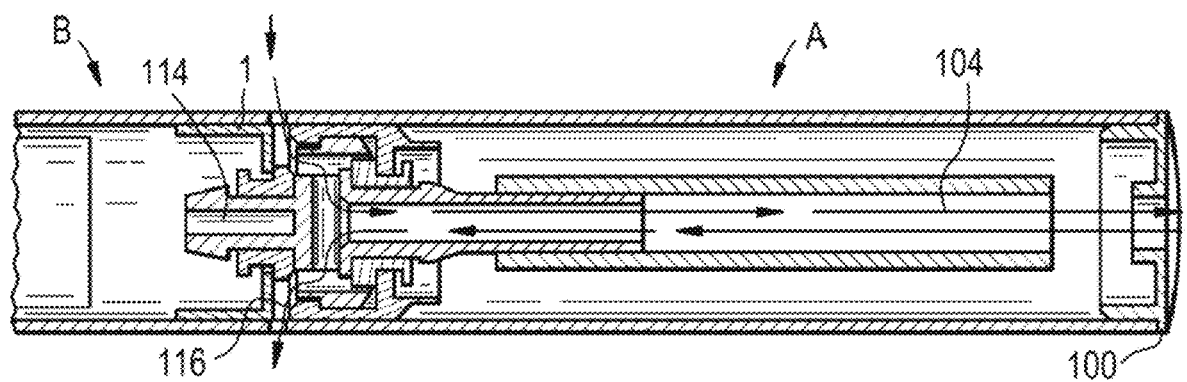
FIG. 16 is a cross-sectional view of an electronic cigarette using the connector and battery post shown in FIGS. 13-15.

The airflow 104 through the connector and battery post combination shown in FIGS. 13-15 is illustrated in FIG. 16. As shown in FIG. 16, one possible draw-back of this arrangement is that upon exhalation, any excess fluid 116 (vapor, saliva, etc.) could be blown through orifice 35, into the pressure differential channel and into the Battery B.

Figure 17:
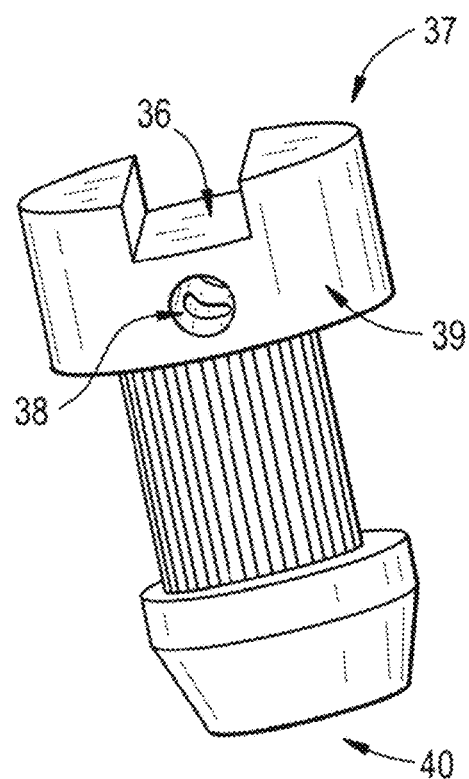
FIG. 17 illustrates an alternative embodiment of a battery post of the present invention.

An alternative embodiment for a battery post designed to minimize this problem is shown in FIG. 17. As shown in this figure, there is no orifice drilled through post head 37. Rather, the air path to the pressure differential channel is created by channel 38 which is drilled beneath groove 36 on the side 39 of post head 37. Channel 38 perpendicularly intersected by the pressure differential channel (not shown) which is drilled longitudinally from battery post end 40.

Figure 18:
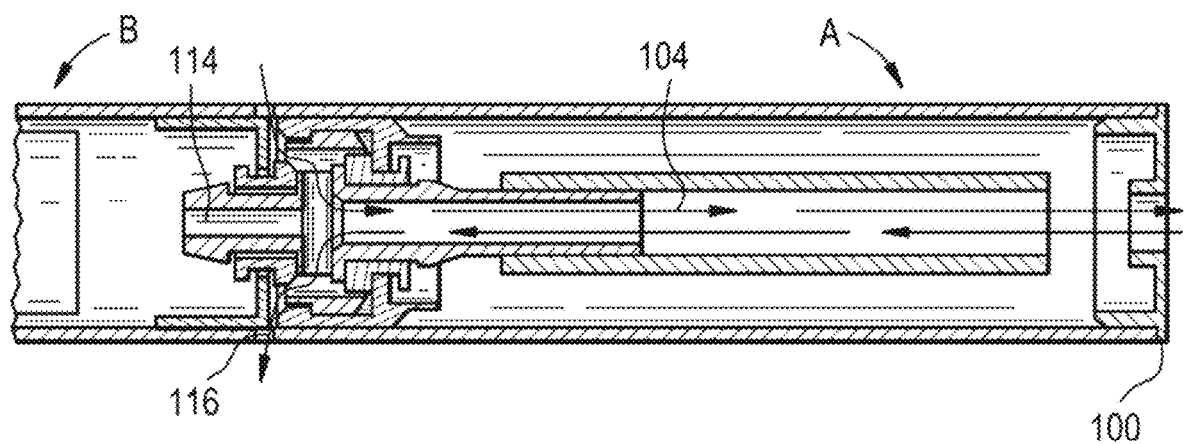
FIG. 18 is a cross-sectional view of an electronic cigarette using the connector of FIG. 13 and the battery post of FIG. 17.

The airflow through a connector such as that shown in FIG. 13 using the battery post shown in FIG. 17 is illustrated in FIG. 18. As is shown in this figure, there is no direct path for excess liquid 116 to migrate into the Battery compartment B.

The connector 1 of the present invention has an additional major advantage in that those embodiments shown in FIGS. 5-18 allow for a substantially silent air-intake without the excessive hissing or noise associated with other known E-cigarettes. Another major advantage of the present invention is its application in newly introduced V-Go and E-go (large-capacity electronic cigarettes) E-cigarettes. V-go and E-go E-cigarettes, which almost always have a side-intake, cannot be used with non-vented female Cartomizers. Heretofore manufacturers always had to resort either to vented female Cartomizers or non-vented male Cartomizers. However, with the present invention, it is possible to create V-go and E-go E-cigarettes that will be interchangeable with Tip-Intake E-cigarettes so that they are compatible with the same existing female unvented Cartomizers, without the need to modify the Cartomizers.

It should be appreciated that although the above-described embodiments demonstrate that some embodiments of the present invention are designed such that the Battery comprises the "male" connection and the Cartomizer comprises the "female" connection, the reverse configuration may be equally suitable, depending on design requirements. Accordingly, the Cartomizer may comprise the "male" connection and the Battery may comprise the "female" connection.

It will be understood that the preferred embodiments of the present invention have been disclosed by way of example and that other modifications and alterations may occur to those skilled in the art without departing from the scope of the disclosure herein.

The invention claimed is:

1. A connector configured to couple a first section and a second section of an e-vaping device, the connector comprising:
 a flange with a first end and a second end;
 a shaft extending from the first end of the flange, an outer shelf being formed by a portion of the first end of the flange;
 a cylindrical base extending from the second end of the flange; and
 an inner shelf within the connector, the cylindrical base and the inner shelf at least partially defining a longitudinal opening,
 the flange defining at least one first notch, the at least one first notch at least partially along the second end of the flange, the at least one first notch at least partially defining at least one first entrance in an outer surface of the flange, the at least one first entrance being an air inlet for at least one first air passage that is in fluid communication with the longitudinal opening.

2. The connector of claim 1, wherein
the inner shelf includes a first surface, and
the first surface at least partially defines an outlet of the at least one first air passage.

3. The connector of claim 2, wherein
the first end of the flange defines a first annular surface that faces the shaft, and
the first surface is aligned with the first annular surface.

4. The connector of claim 1, wherein
the cylindrical base includes sidewalls, and
the sidewalls at least partially define the at least one first entrance.

5. The connector of claim 1, wherein
the cylindrical base includes sidewalls, and the sidewalls and the flange at least partially define the at least one first air passage.

6. The connector of claim 1, wherein
the at least one first notch at least partially defines at least one first entrance in an outer surface of the flange, and
the at least one first entrance is an air inlet for at least one first air passage that is configured to be in fluid communication with the longitudinal opening once the connector connects the first section to the second section.

7. The connector of claim 6, wherein
the cylindrical base includes sidewalls, and
the sidewalls at least partially define the at least one first entrance.

8. The connector of claim 1, wherein
the at least one first air passage has a first longitudinal length that extends in a first direction, and
the first direction traverses through an imaginary cross-sectional line of the connector, the imaginary cross-sectional line passing through a longitudinal axis of the connector.

9. The connector of claim 1, wherein
the cylindrical base includes a third end and a fourth end,
the third end is connected to the flange, and
the fourth end is tapered.

10. The connector of claim 1, wherein the outer surface of the flange is a widest portion of the connector along an imaginary cross-sectional line of the connector, the imaginary cross-sectional line passing through a longitudinal axis of the connector.

11. The connector of claim 1, wherein the inner shelf is configured to hold an electrical contact.

12. The connector of claim 11, further comprising:
the electrical contact, wherein the electrical contact is on an end of the first section.

13. The connector of claim 1, wherein the cylindrical base is configured to connect to the first section, and the shaft is configured to be selectively connectable to the second section.

14. The connector of claim 13, wherein the connector is configured to establish an airflow path once the connector is connected to the first section and the second section, the airflow path causing incoming air to enter the longitudinal opening through the at least one first air passage.

15. The connector of claim 1, wherein
the outer surface of the flange is a widest portion of the connector along an imaginary cross-sectional line of the connector, the imaginary cross-sectional line passing through a longitudinal axis of the connector, and
a first diameter of the cylindrical base is greater than a second diameter of the shaft.

16. The connector of claim 1, wherein the at least one first air passage includes a first air passage and a second air passage that are equidistantly spaced apart on the flange.

17. The connector of claim 16, wherein the first air passage and the second air passage each traverse through the flange at an angle that is about perpendicular to the outer surface of the flange.

18. An e-vaping device, comprising:
the connector of claim 1;
the first section, the cylindrical base of the connector being connected to the first section; and
the second section, the shaft of the connector being configured to be selectively connectable to the second section to connect the first section to the second section.

19. The e-vaping device of claim 18, wherein
the first section is a power section; and
the second section is a cartridge.

20. The e-vaping device of claim 18, wherein the at least one first notch and a distal end of a first housing of the first section combine to at least partially define the at least one first entrance.

21. The e-vaping device of claim 20, wherein the outer surface of the flange, the first housing of the first section and a second housing of the second section combine to form an outer surface of the e-vaping device once the connector connects the first section to the second section.

* * * * *